(12) United States Patent
Harnett

(10) Patent No.: US 11,199,660 B2
(45) Date of Patent: Dec. 14, 2021

(54) SOFT OPTICS WITH MECHANICALLY TUNABLE REFRACTIVE INDEX

(71) Applicant: University of Louisville Research Foundation, Inc., Louisville, KY (US)

(72) Inventor: Cindy K. Harnett, Louisville, KY (US)

(73) Assignee: University of Louisville Research Foundation, Inc., Louisville, KY (US)

(*) Notice: Subject to any disclaimer, the term of this patent is extended or adjusted under 35 U.S.C. 154(b) by 105 days.

(21) Appl. No.: 16/689,597

(22) Filed: Nov. 20, 2019

(65) Prior Publication Data

US 2020/0158544 A1    May 21, 2020

Related U.S. Application Data

(60) Provisional application No. 62/769,623, filed on Nov. 20, 2018.

(51) Int. Cl.
| | |
|---|---|
| *G02B 6/26* | (2006.01) |
| *G02B 6/24* | (2006.01) |
| *G01D 5/353* | (2006.01) |
| *G01L 1/24* | (2006.01) |
| *G02B 6/02* | (2006.01) |

(52) U.S. Cl.
CPC .............. *G02B 6/26* (2013.01); *G02B 6/24* (2013.01); *G01D 5/35367* (2013.01); *G01L 1/242* (2013.01); *G02B 6/02295* (2013.01)

(58) Field of Classification Search
None
See application file for complete search history.

(56) References Cited

U.S. PATENT DOCUMENTS

| | | | | |
|---|---|---|---|---|
| 3,051,003 A | * | 8/1962 | Witt ...................... | G01L 11/025 73/705 |
| 4,295,738 A | * | 10/1981 | Meltz ................... | G01L 11/025 356/32 |
| 4,480,182 A | * | 10/1984 | Ely ....................... | G02B 6/3522 250/227.22 |
| 4,609,816 A | * | 9/1986 | Severin ................. | G01L 1/242 250/227.14 |
| 4,634,858 A | * | 1/1987 | Gerdt ................... | G01L 1/241 250/227.14 |
| 4,691,709 A | * | 9/1987 | Cohen ................ | A61B 5/02154 600/480 |
| 4,701,614 A | * | 10/1987 | Jaeger ................. | G08B 13/186 250/227.14 |
| 4,733,068 A | * | 3/1988 | Thiele .................. | G01L 1/242 250/227.14 |

(Continued)

*Primary Examiner* — Michael Stahl
(74) *Attorney, Agent, or Firm* — W&C IP

(57) ABSTRACT

Embodiments involve optical waveguides with spongy material for cladding or layers that include compressible gas pockets. The refractive index of the porous cladding material will change when compressed, bent, or stretched. Measurements for pressure, strain, bending, etc., may be obtained by monitoring the signal degradation and/or escape of radiant energy, e.g., IR, etc., from the core and out through the spongy cladding, where it may be picked up by a neighboring core. Optical waveguides configured as fibers may be easily sewn to stretchable materials, such as athletic tape, fabrics used in umbrellas, balloons, fabrics used in clothing, etc., to meet a robust number of applications.

15 Claims, 11 Drawing Sheets

(56) References Cited

U.S. PATENT DOCUMENTS

| | | | | |
|---|---|---|---|---|
| 4,781,056 A * | 11/1988 | Noel | ................... | G01L 1/243 |
| | | | | 177/DIG. 6 |
| 4,830,461 A * | 5/1989 | Ishiharada | ............... | G01L 1/243 |
| | | | | 385/13 |
| 5,917,180 A * | 6/1999 | Reimer | .................. | G01L 1/24 |
| | | | | 250/227.14 |
| 6,261,469 B1 * | 7/2001 | Zakhidov | ............... | B82Y 20/00 |
| | | | | 216/56 |
| 2001/0012840 A1 * | 8/2001 | Verbiscar | ................ | A61P 31/22 |
| | | | | 514/164 |
| 2005/0005706 A1 * | 1/2005 | Reichinger | ............. | G01L 1/243 |
| | | | | 73/800 |
| 2013/0335807 A1 * | 12/2013 | Arsenault | ............... | B82Y 20/00 |
| | | | | 359/291 |
| 2016/0334581 A1 * | 11/2016 | Facer | ..................... | G02B 6/264 |
| 2019/0383678 A1 * | 12/2019 | Peele | ..................... | G06F 3/0304 |
| 2020/0400886 A1 * | 12/2020 | Xu | ............................ | G02B 6/125 |
| 2021/0055171 A1 * | 2/2021 | Harnett | .................... | G02B 6/02 |

\* cited by examiner

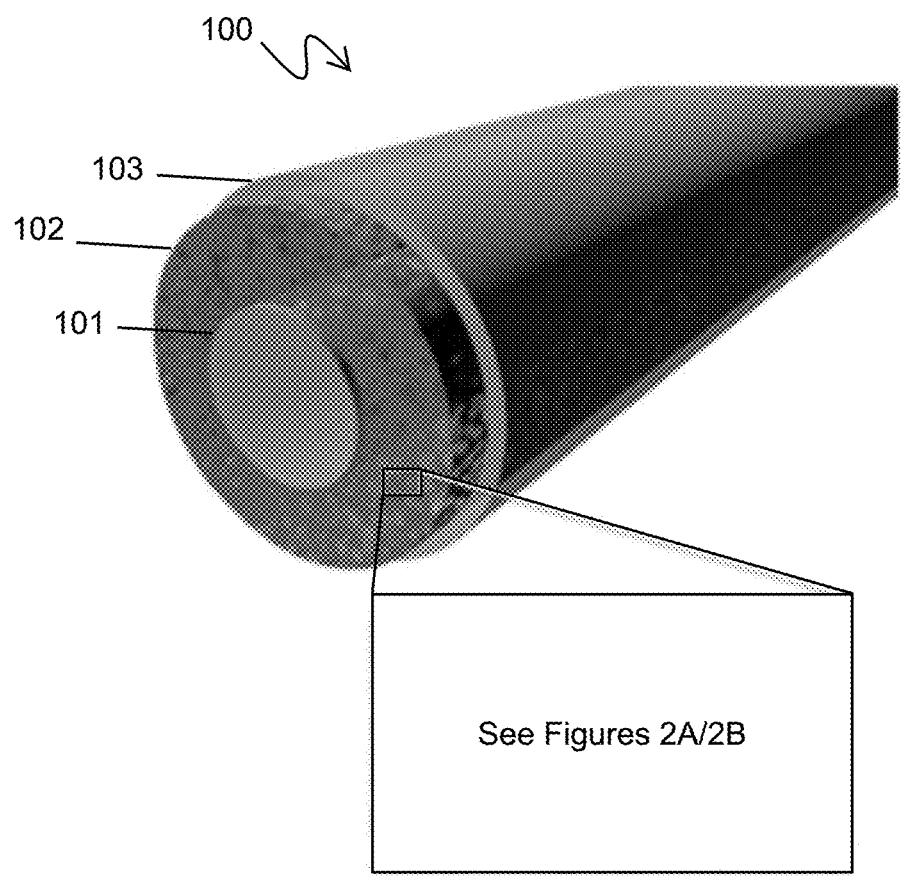
Figure 1
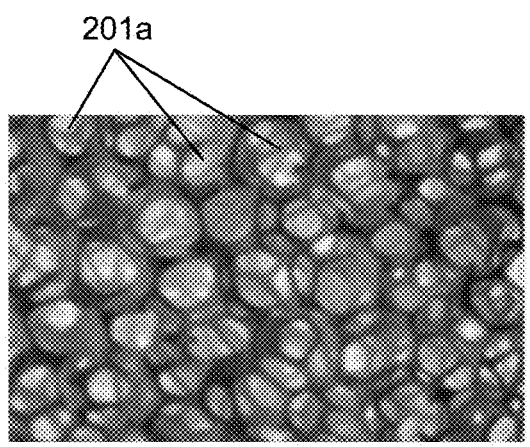 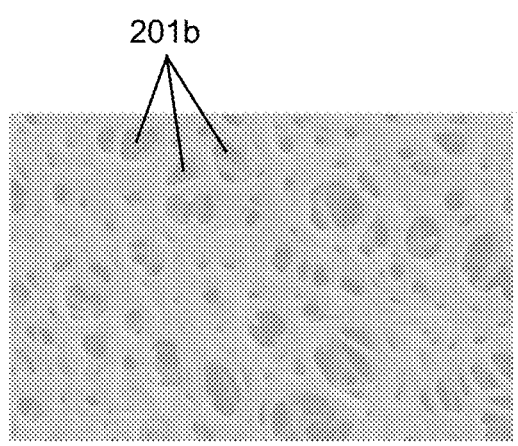
Figure 2A                    Figure 2B

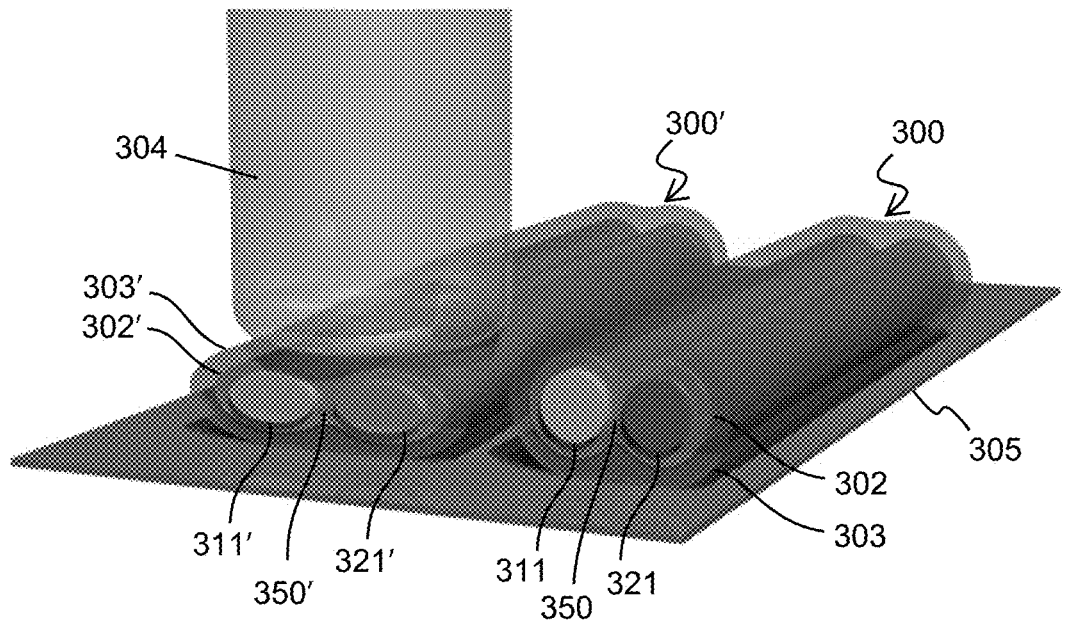
*Figure 3*
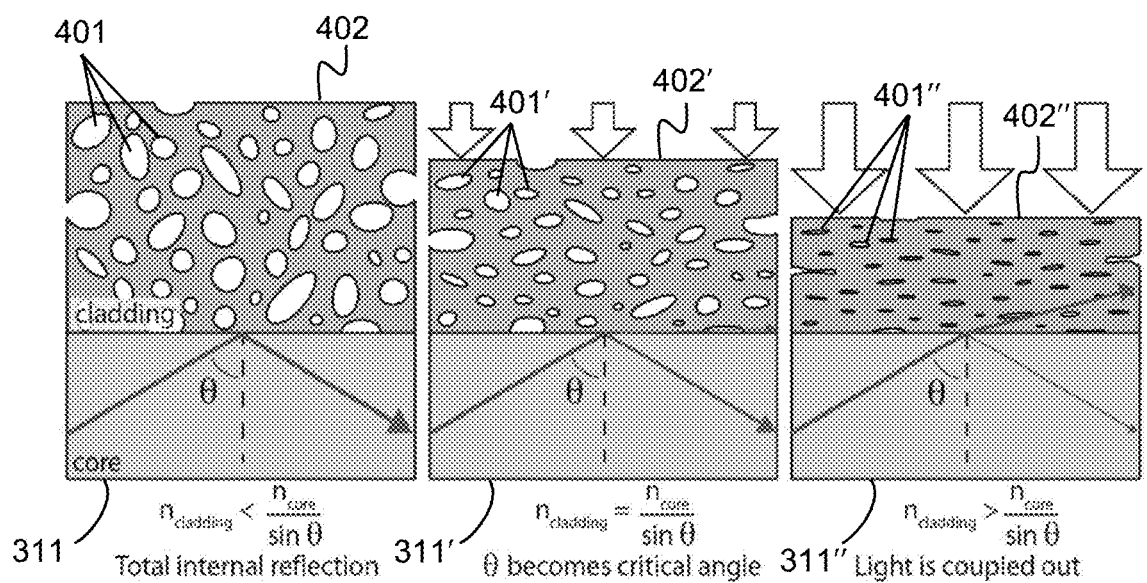
*Figure 4A*  *Figure 4B*  *Figure 4C*

SOFT OPTICS WITH MECHANICALLY TUNABLE REFRACTIVE INDEX

CROSS-REFERENCE TO RELATED APPLICATIONS

This application claims the benefit of U.S. provisional patent application No. 62/769,623, filed Nov. 20, 2018, the complete contents of which are incorporated herein by reference.

FIELD OF THE INVENTION

The invention generally relates to soft optics, and in particular, waveguides and various applications therefor.

BACKGROUND

The refractive index describes the speed of light in a material. Composites made from two or more materials with different indexes of refraction will scatter light at the interfaces between material domains if the domains are on the size scale of the wavelength or larger. However, if the domains are much smaller than the wavelength of the light, the effective refractive index is a volume average of the materials' indexes of refraction. This is sometimes referred to as a "binary optics" principle.

The "binary optics" principle has been applied in brittle dielectrics such as glass containing tiny air-filled pockets. The refractive index of the glass is adjusted at the time of manufacture by setting the amount or size of the pockets in the glass. Of course, after the glass is cooled, the index of refraction of the material is fixed and cannot be subsequently adjusted. Light has been successfully guided in a waveguide that has cladding of "holey" glass with regular or random air holes.

Non-stretchable fiber optic wearables have been used to measure bending and strain of joints but cannot conform to the stretching and twisting of human skin surfaces.

Present technology for highly stretchable strain sensors is based on electrical resistance of conductive polymer composites. Optical signals can cross an air gap, but resistive electronic signals need a continuous conductive path which can be challenging to maintain between a dynamic soft actuator and a rigid detection circuit.

SUMMARY

Some embodiments involve spongy elastic materials with micron, submicron, or nanoscale air pockets that are mechanically compressible to adjust the refractive index at infrared wavelengths. Elastic materials that transmit light and contain air pockets smaller than the wavelength of that light can act as tunable "metamaterials" with a variable refractive index. The refractive index describes the speed of light in a material. When light passes through a collection of structures made from different materials, if the structures are much smaller than the wavelength of the light, the effective refractive index is a volume average of the materials' index of refraction. A clear deformable rubber may have an index of refraction of ~1.4, whereas air pockets may have an index of refraction of ~1. When the material is subject to pressure, the air pockets compress to take up a smaller fraction of the total volume, and the overall refractive index of the spongy material increases.

Spongy materials may be incorporate as a cladding in a polymer waveguide. As the waveguide is compressed, more light will escape as the index of the cladding increases relative to the index of the waveguide core. Under pressure, light that was once reflected from the interface can scatter out to be measured as a loss signal. The lost light can be picked up by a sensor or another fiber, sending it along a new path. In some embodiments, a pair of parallel fibers may share a spongy cladding. One fiber may be lit and the other dark. Only under compression is light from the lit fiber leaked to the dark fiber. The light in the dark fiber may then be detected to quantify the leakage.

Optical waveguide and fiber devices according to this disclosure may include a detector which has a radiant energy receiver (e.g., a photodiode, CMOS sensor, CCD sensor, etc.) positioned at one end of one of one or more optical fibers. The detector detects changes in an amount of radiant energy transmitted from another end of the one or more optical fibers. A radiant energy detector may be positioned at a side of an optical fiber so that the detector detects radiant energy exiting the core of a fiber. In short a detector may be arranged to detect changes in radiant energy passing through a core or escaping a core.

Optical devices employing a spongy elastic material with a variable pressure-sensitive index of refraction have a variety of further exemplary applications. One exemplary application is detection of changes in the shape of inflatable structures, such as habitats, weather balloons, bounce houses, and soft robots. Another exemplary application is monitoring patients' physical activity noninvasively using bandages. Another exemplary application is motion capture. Another exemplary application is stretchable optical communication links for digital data in body area networks. Another exemplary application is detecting sudden changes in the tension of wires caused by fallen branches, damaged equipment or tripping, so electricity can be timely shut off for safety. Another exemplary application is detecting length changes in musical instrument strings for amplification. Another exemplary application is measuring the sequence of deployment of lightweight fabric structures like tents, awnings, and parachutes. Another exemplary application is sensing the location and amount of pressure on a surface for human-computer interface applications.

Applications include optical sensors, including sensor arrays that capture both spatial and intensity information about mechanical signals (pressure, stretching, bending) in a region. Some embodiments may use pressure-induced fiber-to-fiber light coupling to collect spatial information. Waveguide based sensors consisting of stretchable materials may be used to conform to the stretching and twisting of human skin surfaces.

BRIEF DESCRIPTION OF THE DRAWINGS

FIG. 1 is a drawing of an optical waveguide with spongy elastic cladding.

FIG. 2A is a photograph of a first example spongy material.

FIG. 2B is a photograph of a second example spongy material.

FIG. 3 is a schematic of a fiber pair usable for spatial sensing at lower pressures using a mechanically responsive spongy cladding.

FIGS. 4A, 4B, and 4C are diagrams showing portions of a solid core and adjacent spongy cladding under different levels of pressure/compression.

DETAILED DESCRIPTION

Figure 2C:
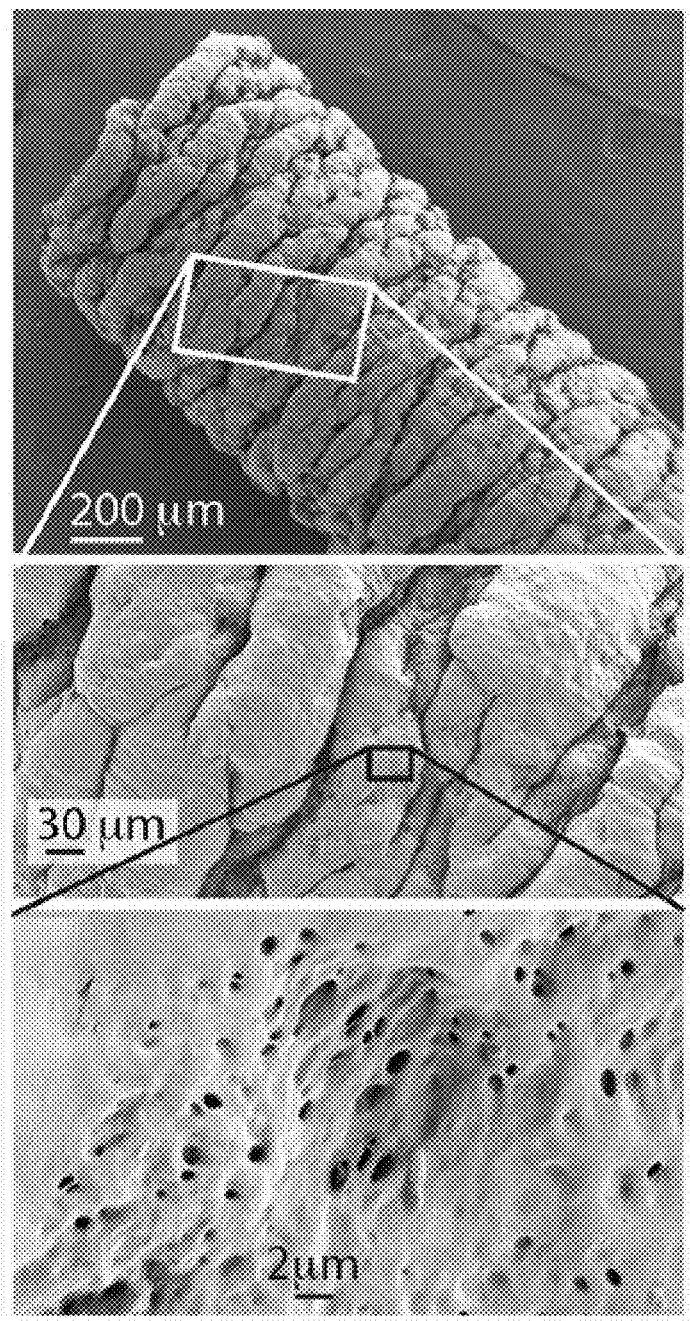
FIG. 2C is a compilation of successively magnified images of the surface of an optical fiber cladding which has micropores.

FIG. 1 shows an optical device, in particular an optical waveguide 100. The waveguide 100 may be but is not limited to an optical fiber. The waveguide 100 comprises a core 101, a cladding 102, and a jacket 103. The cladding may encase the core, and the jacket may encase both the core and cladding. The core polymer may be a thermoplastic polymer. The core polymer may be (but is not limited to) polylactic acid (PLA), ethylene vinyl acetate (EVA), and thermoplastic polyurethane (TPU). The cladding may be a polymer such as but not limited to paraffin wax (PW) or polyethylene glycol (PEG). The core and the cladding may be the same base material (e.g., the same thermoplastic polymer), though the core is solid (does not have air pockets) and the cladding spongy (with many air pockets). "Core" is used to refer to the primary light transmissive element of the waveguide. A waveguide's core may be its geometrically centered material/structure but need not necessarily be at the geometric center. A single waveguide may have a single core or multiple cores. Generally, "waveguide device" as used herein is a device that may employ a plurality of waveguides or waveguide cores. A center structure of a device that is substantially unsuitable for ever transmitting light, despite being at a geometric center of the device, is not a "core" per that term's usage in this disclosure.

The surface or surfaces of a core where it interfaces with a cladding may be modified during manufacture to control waveguiding and scattering. For long-distance waveguiding a low refractive index, smooth coating is sometimes desired, while for scattering light into or out of the waveguide core, a rough surface may be desired.

FIGS. 2A and 2B show close-ups of non-limiting examples of transparent spongy elastic material suitable for use for the cladding 102 of optical devices according to this disclosure. The spongy elastic material comprises air pockets 201*a* (FIG. 2A) or 201*b* (FIG. 2B). The air pockets may vary in size from one another and may but need not necessarily be independent of one another. That is to say, some air pockets may adjoin neighboring air pockets. Exemplary spongy materials include both open-cell foams and closed-cell foams made from incompressible polymers. "Air pockets" as used herein may contain any of a variety of compressible gases or mixtures of gases or other compressible materials or mediums. Ambient air is but one possibility. "Pockets" is used to describe spaces which are generally surrounded by solid material like an elastomer. Pockets may be sealed (e.g., as in closed cell foams) or not sealed (e.g., as in open cell foams) from the environment by the surrounding solid material. Pockets may alternatively be called voids or pores, and a material having the same may be called porous. Air pockets may be regular or random holes. For convenience of discussion, "air pockets" will be used in this disclosure but other suitable terminology consistent with this disclosure may be employed in the practice of the invention. Air pockets or pores may be within a 1-2 micron diameter range, submicron (collectively averaging less than or equal to a micron), or less than 500 nm. Air pockets or pores may be micro- and/or nano-structured. Air pockets or pores may be of substantially uniform size/monodisperse, or not, depending on the embodiment and method of manufacture. Distribution of pockets or pores may be relatively uniform in some embodiments and more variable other embodiments.

FIG. 2C offers yet another non-limiting illustration of porous cladding material. A side view of an optical fiber is shown with successive magnification until micropores at the surface of the cladding are visible. Cores may be covered with hierarchically structured coatings formed on the surface of the cores.

FIG. 3 shows an optical waveguide device 300 comprising a first waveguide core 311 and a second waveguide core 321. The cores 311 and 321 share a cladding 302 comprising or consisting of a spongy elastic material. The spongy material comprises or consists of an elastomer and air pockets. The air pockets are compressible. The elastomer is deformable but not substantially compressible, with the result that the volume of the elastomer is relatively constant despite the spongy elastic material to which it belongs having a variable volume depending on applied external forces. The device 300 may be attached or fixed (e.g., by sewing) to a support material 305. The support material 305 may be a stretchable material such as an athletic tape.

The spongy elastic material of cladding 302 has a refractive index which changes when the spongy elastic material is compressed, bent, or stretched. The cladding may be but is not necessarily transparent or semi-transparent in all cases. That is, in some cases, the cladding may be relatively opaque. A portion 350 of the spongy elastic material is positioned between the first and second waveguide cores 311 and 321. The portion 350 may define the total separation between core 311 and core 321. The portion 350 may be in direct contact with the core 311 on one side and core 321 on the other side. The cores 311 and 321 may sandwich the portion 350 of the spongy elastic material. The portion 350 may completely fill the shortest distance between core 311 and core 321. The portion 350, in a relaxed (i.e., uncompressed) state may be between 1 mm (generally corresponding with a stylus tip size) and 2 cm (generally corresponding with a fingertip size) in size. The cladding 302 other than the portion 350 may in some embodiments not be transparent or may not be spongy and may not allow leakage even under compression. The jacket 303 may or may not permit passage of some light (e.g., leakage) whether or not under compression. Total diameter of filament or fiber based embodiments may be (but are not limited to) 1 mm diameter.

In an absence of external forces, the first waveguide core 311 transmits a first amount of radiant energy (light) whereas the second waveguide core 321 transmits a different amount of radiant energy, for instance no radiant energy (no light;

core 321 is dark). Source of radiant energy (not shown in FIG. 3) may vary, but one non-limiting example is one or more LEDs, e.g., an infrared LED.

FIG. 3 uses a prime symbol (') to identify an element that is under an external force, generally a source of pressure which may cause compression. In FIG. 3, an external force applicator 304 is depicted applying a force to waveguide device 300'. In practice, the external force applicator 304 may be virtually anything capable of putting force on something else, including but not limited to part of a person (e.g., a finger). At or above a certain threshold of compression, a variable non-zero fraction of radiant energy in the first waveguide core 311' escapes to the second waveguide core 321' through the spongy elastic material of cladding 302' (in particular, through portion 350' which is between the two cores 311' and 321'). The fraction of energy that escapes depends on the refractive index of the spongy elastic material. Since the refractive index of the spongy elastic material depends on the degree of compression thereof, the fraction of energy that escapes from the first core 311' to the second core 321' depends on the degree of compression.

Sensor waveguide devices may vary in size, but there are appreciable differences between long-distance communication optical fibers and waveguide devices and fibers which are used for robotics or human health, for example. Communication optical fibers may be more than a kilometer long. A sensor fiber according to some embodiments herein, by contrast, may be less than 30 cm in length, e.g., approximately 10 cm. The comparatively short distance of waveguide devices according to sensing applications makes excessive light loss a substantially lesser concern, allowing for prioritization of other parameters such as mechanical performance. Total length of waveguide devices according to this disclosure may vary during use because of the highly elastic materials employed. A waveguide device may be stretched, for example, to greater than 4× its original length without breaking. The stretchiness of waveguides disclosed herein makes the technology well suited for wearable sensors that detect changes in length and pressure.

FIGS. 4A, 4B, and 4C are diagrams showing portions of a solid core and adjacent spongy cladding under different levels of pressure/compression. In this exemplary embodiment, the spongy cladding is a closed-cell foam made from, for example, an incompressible rubber. The elastomer volume therefore stays constant under compression, whereas air in the air pockets compresses or else exits at the sides of the spongy cladding if it finds a path through the foam. To cause a pressure-induced light leak in the waveguide, the cladding material should have an index of refraction that starts out lower than that of the core and which increases in response to pressure. Steeply angled light will begin to leak if there is any increase in the cladding index, while if the cladding gains a higher index than the core, there will be no total internal reflection for light in the core at any angle.

In FIG. 4A, the spongy cladding material 402 and the solid core material 311 are under no external loading. Air pockets 401 are at their largest respective volumes. For clarity of illustration, only three air pockets are labeled but many are apparent from the drawing. In this relaxed configuration, the index of refraction of the cladding ($n_{cladding}$) is significantly less than the index of refraction of the core ($n_{core}$). As a result light in the core 311 exhibits total internal reflection at the core-cladding interface.

In FIG. 4B, pressure has been applied to the spongy cladding material 402' and the solid core material 311'. (As with FIG. 3, the prime symbol (') is used to denote subjugation to a non-zero amount of external force which may be causing compression; in FIG. 4C, double prime (") is used to denote subjugation to a still greater amount of applied force.) As visibly apparent from the drawings, compressed air pockets 401' are smaller in volume than uncompressed air pockets 401. The change in volume of the air pockets as a result of the compression results in a change in the index of refraction of the cladding material 402'. The angle of incidence θ becomes the critical angle when $n_{cladding} = n_{core} / \sin θ$. FIG. 4B represents a threshold condition in which any further compression will begin to result in substantial leakage of light from the core.

In FIG. 4C additional compression of the spongy cladding material 402" has occurred, resulting in still further reduction in the volume of compressed air pockets 401". As the cladding material 402" is deformed, its optical density increases by void compression. The index of refraction of the cladding ($n_{cladding}$) is now greater than the index of refraction of the core ($n_{core}$) divided by the sine of the angle of incidence (θ). Light is therefore coupled out from the core 311".

Different structured elastomers with different mechanics may be employed in different embodiments for the spongy material of claddings. Pressure-dependent optical fibers may be "tuned" depending on the particular elastomer and the mechanical structure of such elastomeric material made from the elastomer. With larger structures (1 micron range and up, when using infrared light), random scattering at rough surfaces will vary as features deform under pressure, while submicron structures will have a pressure-dependent effective index of refraction $n_{eff}$ that is proportional to average material density.

The effective refractive index $n_{eff}$ of an open-cell material with sub-wavelength pores is determinable by taking a spatial average of the indexes:

$$n_{eff} = n_a + f_s(n_s - n_a)/(1-c) \tag{1}$$

where $n_a$ is the refractive index of the air or other material that fills the open-cell pores, $n_s$ is the refractive index of the incompressible polymer, $f_s$ is the volume fraction occupied by the polymer before compression, and c is the change in volume divided by the original volume.

Figure 5:
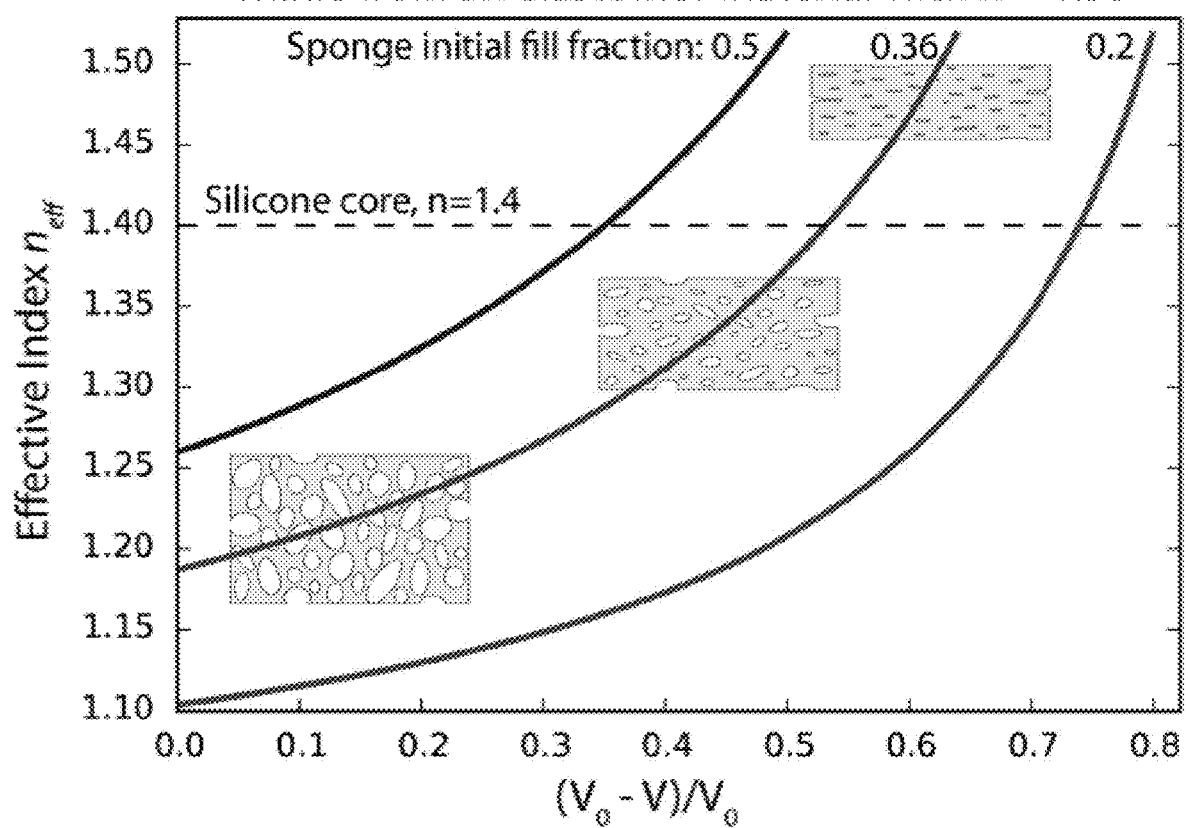
FIG. 5 is a density-based model of effective refractive index as a function of compression.

In FIG. 5, the effective index from Equation 1 is plotted for foams with three different starting fill fractions; when fully compressed, all three traces hit the maximum solid polymer index of 1.53. The dashed line at n=1.4 represents the index of refraction of the solid core. The core's index of refraction does not vary significantly with compression. To cause a pressure-induced light leak in this waveguide, the material should have an index of refraction that starts out lower than that of the core, and increase (not necessarily crossing 1.4) in response to pressure. An exemplary structure is a sub-100 nm feature size foam (for low scattering at IR wavelengths) with a polymer volume fill fraction in the 0.5 range, and with a solid polymer refractive index in the 1.45-1.55 range.

An exemplary spongy material for use with some embodiments is a closed-cell foam. Close-cell foams are suited for modeling as compressible air volume in series with a fixed-volume solid polymer. Unlike gases in open-cell networks, gases trapped in closed cells compress. For gases compressed to half their volume from atmosphere, the refractive index increase is only in the sub parts per thousand range, making Equation 1 approximately correct despite gas compression. The main difference in mechanical performance of closed-cell foams is lower compressibility due to the trapped gases exerting pressure on the polymer.

Figure 6A:
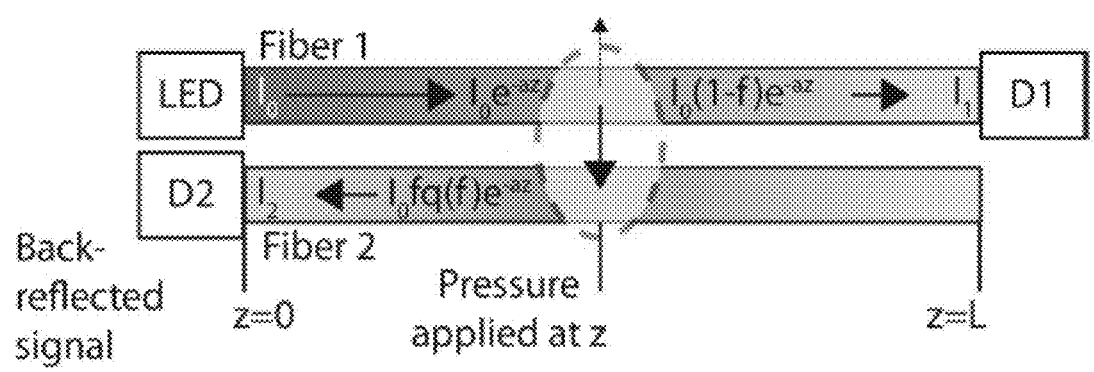
FIG. 6A is a fiber pair schematic.

FIG. 6A is a schematic of an optical waveguide device consistent with the description above for FIG. 3. Here, the optical waveguide device is configured as a location-aware pressure feedback device. An LED acts as a source for Fiber 1 at a first end. A detector D1 detects radiant energy at the far end of Fiber 1, opposite the first end. A detector D2 is arranged to measure a back-reflected signal in the core of Fiber 2, wherein an intensity of the back-reflected signal varies in dependence on a spatial position where the spongy elastic material is compressed, bent, or stretched. The intensity of the injected light from the LED source is $I_0$. The intensity of the signal detected by detector D1 is $I_1$. The intensity of the back-reflected signal detected by detector D2 is $I_2$. The range of locations where pressure is detectable is z=0 to z=L, with L being the length of both waveguide cores. L is also the distance between the LED source and detector D1. Pressure is applied at z, with z being any value from 0 to L.

Without coupling between the fiber cores, the light intensity I in Fiber 1 as a function of z is determinable using the Beer's Law transmission model:

$$I = I_0 e^{-az} \quad (2)$$

where a is a constant (the attenuation coefficient), $I_0$ is the initial intensity, and I is the intensity after light travels a distance z through the core. When the fiber pair of the waveguide device is compressed at point z, there are two effects: 1) the spongy cladding has an increased index of refraction, and 2) at sufficiently high pressures, light encounters the deformed interface at a steeper angle than before. Both effects allow some light to escape the core of Fiber 1, and some of that light crosses into the other fiber.

In the model depicted by FIG. 6A, when the fiber pair is pressed at point z, a fraction f of the light intensity is lost from Fiber 1, and some fraction of that lost light, q(f), is gained by Fiber 2. The loss fraction f is expected to increase monotonically with pressure, and the relationship q(f), describing the fraction of lost light that is picked up by the unlit Fiber 2 for a given value of f, is a function of the fiber materials and geometry. Because the fiber materials and geometry are predeterminable, q(f) is predeterminable.

FIG. 6A shows two different detectors D1 and D2. Detector D1 is arranged to detect signal intensity at the far end of Fiber 1. The far end is opposite the source. In this example the source is one or more light-emitting diodes (LED), but alternative sources (e.g., laser, LED array, etc.) may be used in other embodiments. Detector D2 is arranged to detect signal intensity at the near end of Fiber 2. For parallel fibers, the near end of Fiber 2 corresponds spatially with the near end of Fiber 1. Similarly, the far end of Fiber 2 corresponds spatially with the far end of Fiber 1.

The intensity signal $I_1$ at the far end of Fiber 1, detectable with detector D1, is usable to determine only pressure information, contained in f.

$$I_1 = I_0(1-f)e^{-aL} \quad (3)$$

The intensity signal $I_2$ at the near end of Fiber 2, detectable with detector D2, is usable to determine both pressure and spatial information:

$$I_2 = I_0 f q(f) e^{-2az} \quad (4)$$

After measuring both intensity values $I_1$ and $I_2$, the loss fraction f is extractable from Equation 3. The loss fraction f is then usable to look up the pressure, and q(f) is obtained from pre-determined fiber characterization data (e.g., with a lookup table). Finally the z-location where the pressure and thus the light loss occurs is determined from Equation 4.

While a variety of light sources may be employed in different embodiments, it is desirable to select a wavelength range of a light source based on the size range of the air pockets in the spongy elastic material. Sub-wavelength voids (<500 nm diameter for visible light) may potentially create mechanically tunable optical materials, while larger structures will couple light into and out of the core by scattering. Generally, the material domains are selected to be smaller than the wavelength of the light such that the effective refractive index is a volume average of the indexes of refraction of the composition (the composition comprising at least elastomer and compressible gas). In an exemplary embodiment, the pore size may be 500 nm or smaller or 450 nm or smaller, and the source may be at least 500 nm or at least 450 nm, e.g., a visible light source (e.g., in the range 500-700 nm, or 450-700 nm), or in some instances preferably at least 700 nm or greater, e.g., an infrared light source (in the 700 nm to 1 mm range).

Figure 6B:
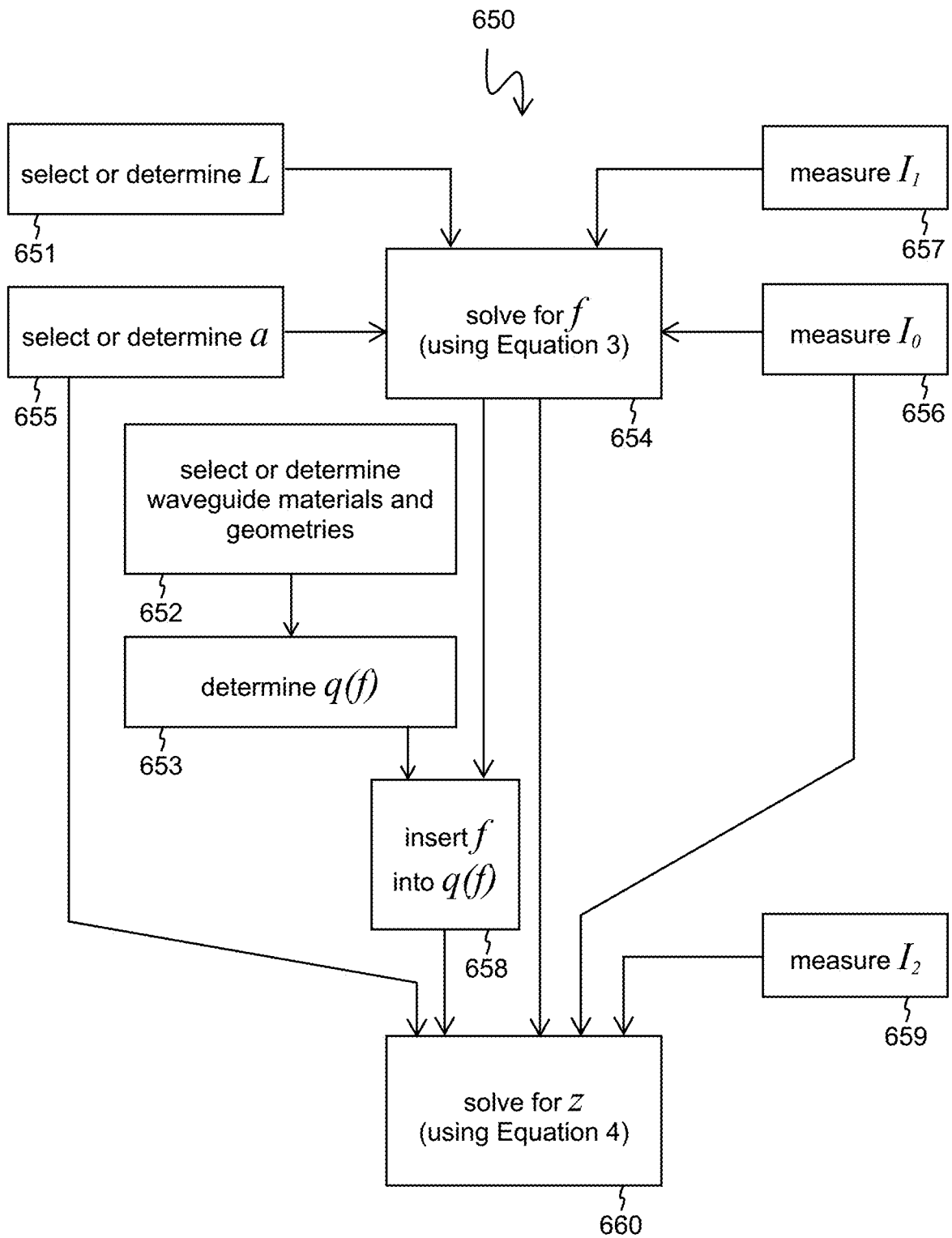
FIG. 6B is a flowchart of a method of detecting a position of externally applied pressure with an optical waveguide device.

FIG. 6B provides a visual flowchart of a method 650 corresponding to the preceding description which allows for determination of a position of externally applied pressure with an optical waveguide device. While FIG. 6A referred to fibers, FIG. 6B will use the broader terminology of "cores" since not all waveguides/waveguide cores are necessarily configured as fibers in all embodiments.

The length L of the optical waveguide device as well as the waveguide materials and geometries are selected or determined at blocks 651 and 652, respectively. These physical parameters may be selected at the time of manufacture for a particular application or use. For an end user that does not necessarily manufacture, such physical parameters may be obtained from the manufacturer or ascertained experimentally. From the waveguide materials and geometries 652, q(f) may be determined at block 653. The function q(f) is constant for a completed waveguide device subject to no further manufacturing. Recall that f is the fraction of light intensity lost from a "lit" fiber when it is subject to pressure/compression, and that q(f) is the fraction of light lost from the "lit" first fiber that is picked up by the "unlit" second fiber for any given value off.

The fraction of light lost from a lit fiber at any given time is determinable using Equation 3 at block 654. Equation 3, given above, requires the constant a from block 655 and the length L from block 651. The length L may be a constant, or it may require determination with a length measuring device if the waveguide device is capable of and subjected to elongation. Two light intensities are also needed to solve for f at block 654. The intensity of light $I_0$ injected at a first end of the "lit" fiber is measured or predetermined at block 656. The intensity of light $I_1$ reaching the far end of length L of the core is measured at block 657 with a detector.

With the formula q(f) from block 653 and numerical value f from block 654, the latter is inserted into the former at block 658 to determine the numerical fraction of light lost from the first core that is captured within the second core. The intensity of light $I_2$ back-reflected in the second core along the length L is detected at block 659 with another detector. The position or location z where the light switches cores, corresponding with the position or location where pressure was applied, is finally determined at block 660 using the values from block 654, 655, 656, 658, and 659.

Figure 7:
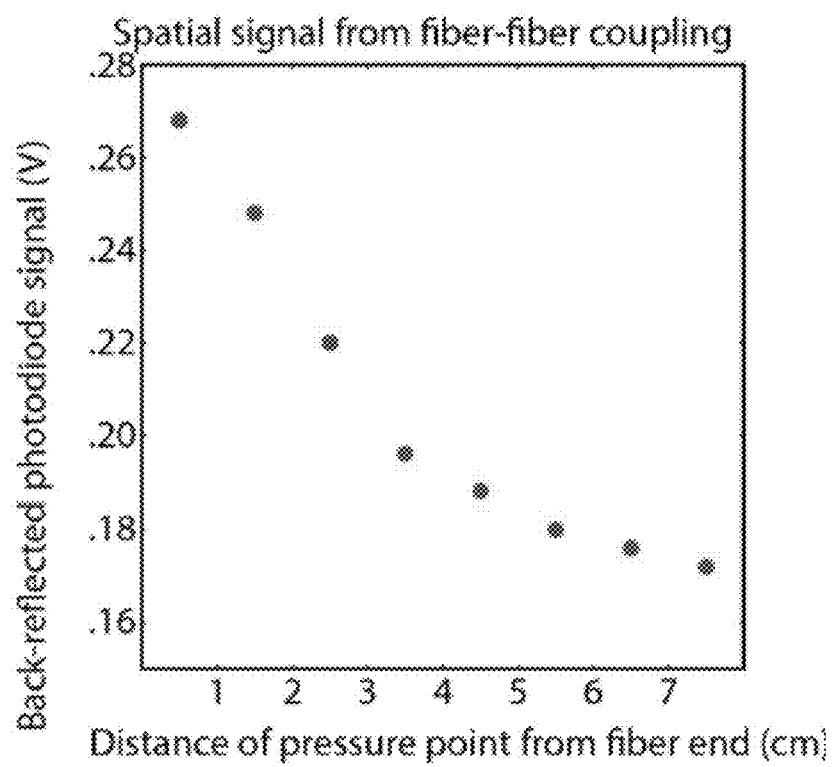
FIG. 7 is a diagram of spatial signal from fiber-fiber coupling.

FIG. 7 shows sample test data that exhibits spatially dependent intensity signal from pressing on a solid deformable optical fiber pair at >10 PSI. The parallel fiber pair was sewn on fabric with both fibers having solid elastomeric claddings. The fibers cross-couple light when pressed, leading to a monotonic intensity signal as a function of distance.

The optomechanical properties of the test prototype yielding the data in FIG. 7 were such that relatively high pressures were required to induce leakage and optical coupling. However, different embodiments may be configured to have different sensitivity levels. For instance, some embodiments, may be tuned to react and sense pressures and forces consistent with human touch or changes in scale consistent with human body.

Figure 8A:
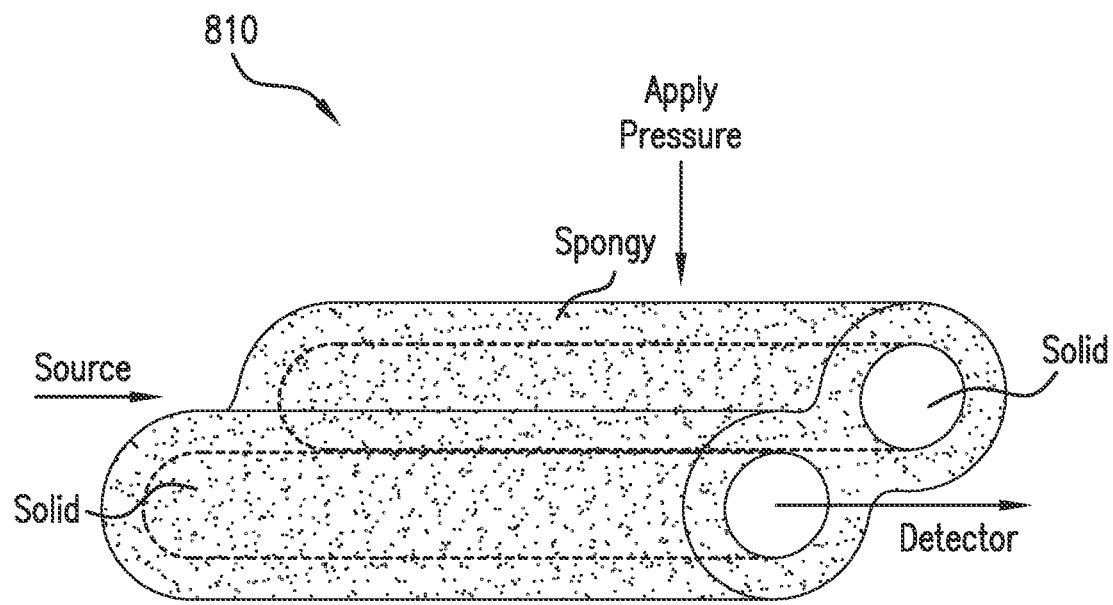
FIG. 8A illustrates parallel cylindrical core-core coupling.

FIGS. 8A, 8B, 8C, and 8D provide illustration of non-limiting variations in the configuration of cores and spongy elastic material. FIG. 8A generally corresponds to FIG. 3. The device 810 comprises at least two cores which are configured as fibers and arranged in parallel with shared spongy elastic material cladding encasing both cores.

Figure 8B:
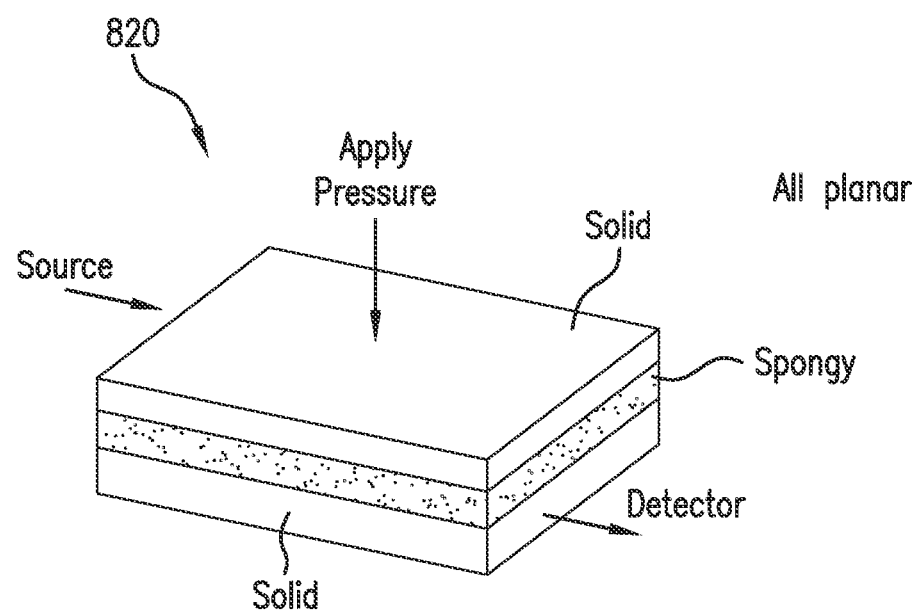
FIG. 8B illustrates parallel film core-core coupling.

FIG. 8B is a device 820 with cores arranged as planar layers or films (e.g., thin films) spaced apart by a spongy elastic material planar layer or film.

Figure 8C:
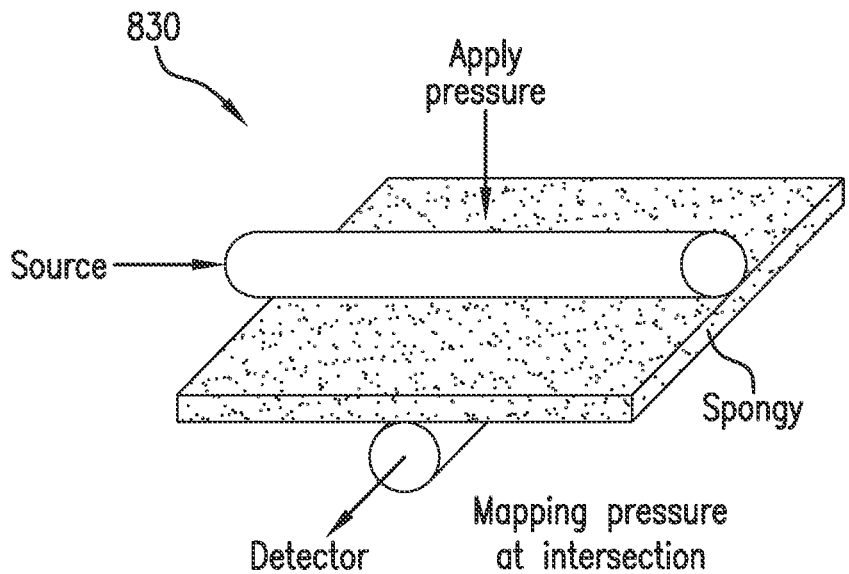
FIG. 8C illustrates non-parallel cylindrical core-core coupling.

FIG. 8C is a device 830 in which the plurality of cores are configured as fibers, but the fibers are not all parallel. Any two fibers may be arranged at a perpendicular angle, or alternatively at any angle between 0 and 90°. Some of the fibers may nonetheless be parallel, whereas others are at angles; see, for example, FIGS. 9A and 9B. The fibers are separated by the spongy elastic material which may form a planar layer between the fibers (the fibers may be embedded within the spongy elastic layer). The path of light in such an embodiment may vary in three dimensions. As illustrated, source light in a first lit fiber may travel in an x-direction, may escape under pressure in a z-direction to reach the second fiber, and may travel in a y-direction after being capture by the second fiber. Primary axes of an x-y-z coordinate system offer an easy to follow illustrative example, but in practice the paths defined by fibers and their spongy elastic couplings may vary considerably in three-dimensional space and described according to different coordinate systems.

Figure 8D:
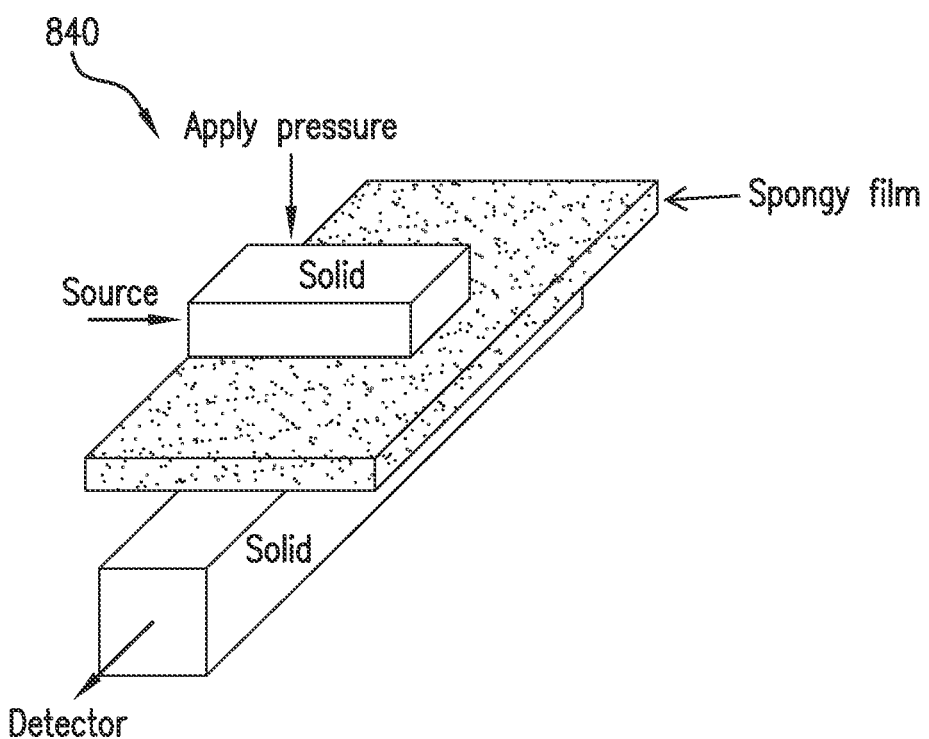
FIG. 8D illustrates non-parallel non-cylindrical core-core coupling.

The device 840 in FIG. 8D is much the same as device 830 in FIG. 8C, except that the device 840 illustrates that a variety of cross-sectional shapes and configurations may be employed for the cores/fibers. In device 840, the fibers are polygonal, in particular rectangular or square, in cross-section. That is, fibers may be cylindrical in some embodiments and non-cylindrical in other embodiments.

Other variants on the approach in FIG. 6A include fibers that do not have the same length, with equations modified accordingly. With different fiber lengths, a detector may be placed at the far end of Fiber 2 to collect both pressure and spatial information.

Figure 9A:
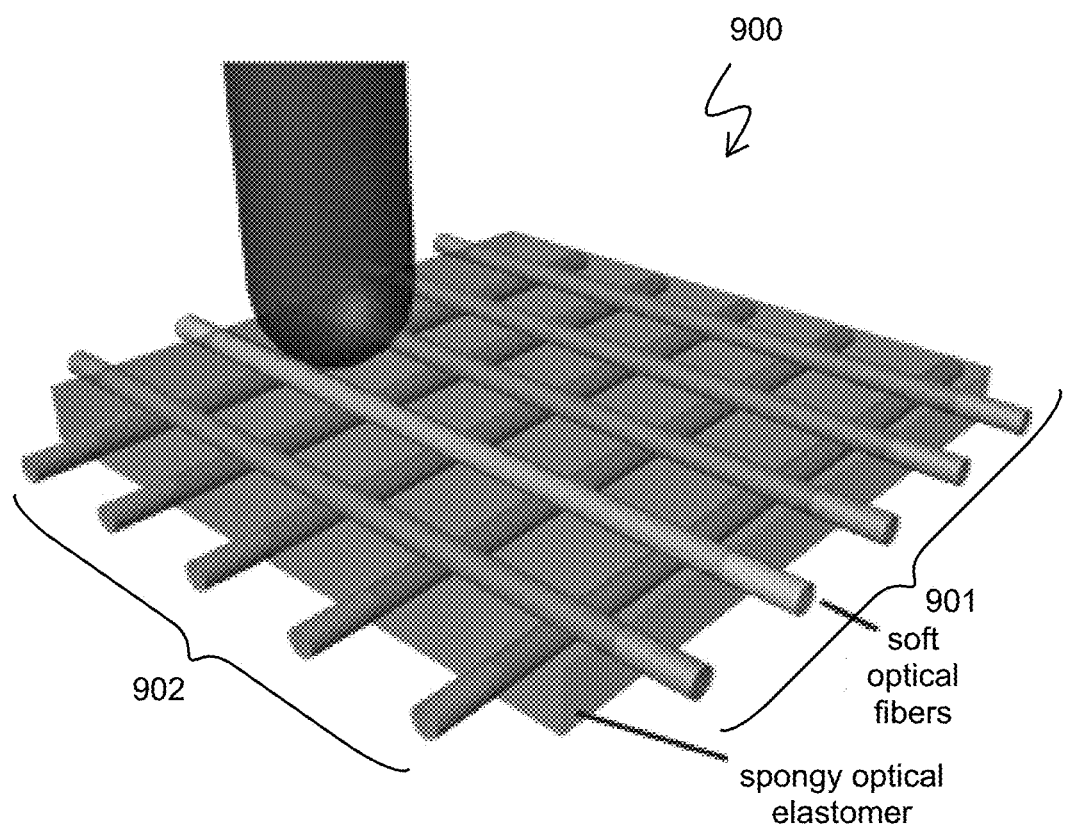
FIG. 9A is a grid sensor for spatial mapping in two or three dimensional space.
Figure 9B:
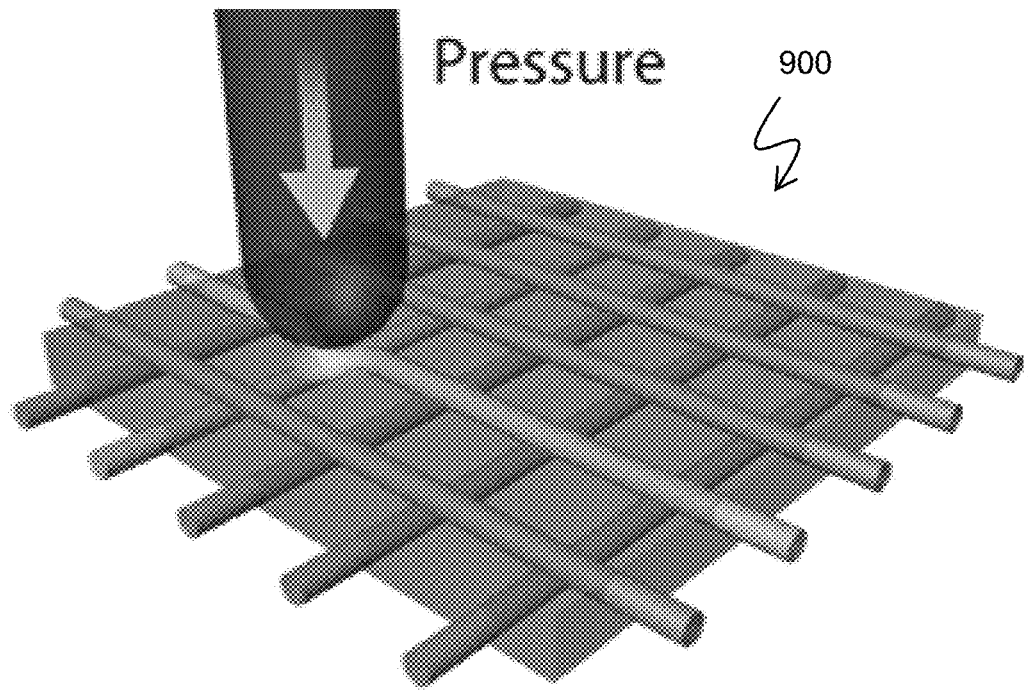
FIG. 9B shows an application of pressure and resultant coupling between row and column fibers for the grid sensor of FIG. 9A.

To capture more complex spatial data such as pressure applied over a section instead of a point source, or pressure applied at multiple positions simultaneously, a scanned grid approach may be implemented using the spongy elastomer. FIGS. 9A and 9B show row and column fibers embedded in a spongy optical elastomer matrix. Rows are lit one at a time using an electronic circuit, and light leaks into columns if pressure has been applied at the lit row-column junction. A sensor at the end of each column measures light intensity, which depends on pressure and on the known distance from the junction to the sensor.

According to the embodiment illustrated by FIGS. 9A and 9B, an optical waveguide device 900 may comprise a first group 901 of waveguide cores arranged in rows in a first geometric plane; a second group 902 of waveguide cores arranged in columns in a second geometric plane spaced apart from the first geometric plane; a spongy elastic material with compressible gas pockets therein, wherein the spongy elastic material has a refractive index which changes when the spongy elastic material is compressed, bent, or stretched, wherein the spongy elastic material is positioned between the first and second groups of waveguide cores, wherein radiant energy in the first group escapes to the second group through the spongy elastic material depending on the refractive index of the spongy elastic material; and one or more detectors arranged to detect changes in one or more signal intensities in the second group of waveguide cores which depend on the radiant energy that escapes the first group through the spongy elastic material when the spongy elastic material is compressed, bent, or stretched. The optical waveguide device may further comprise one or more processors configured to cause sequential illumination of waveguide cores in the first group one at a time; and determine a spatial position where the spongy elastic material is compressed, bent, or stretched based on a first signal intensity from a waveguide core from the first group that is illuminated and a second signal intensity from a waveguide core from the second group for which a change in signal intensity is detected.

Figure 10A:
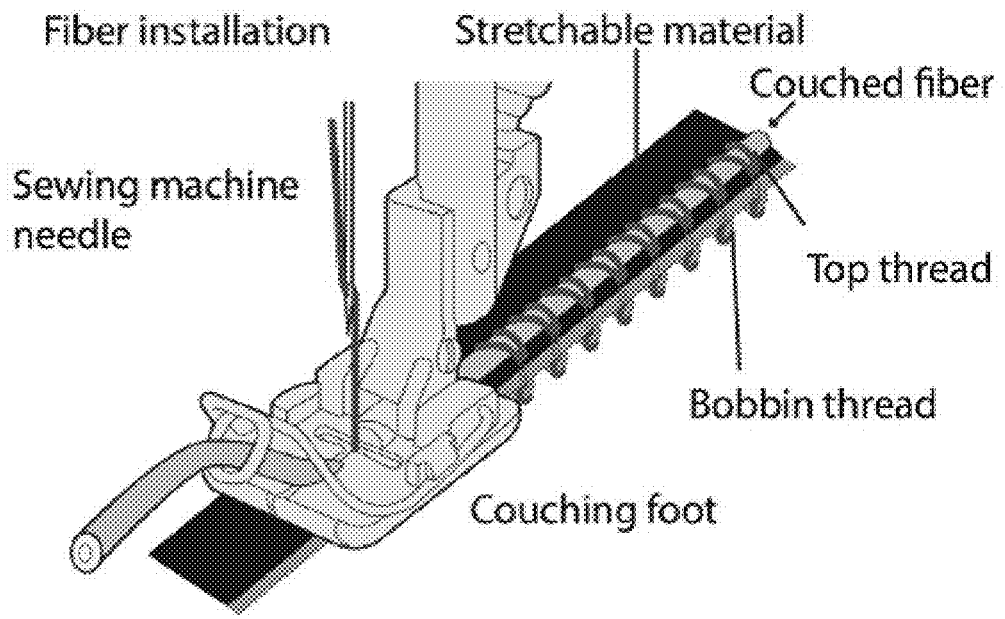
FIG. 10A illustrates an optical waveguide installation by sewing.

FIG. 10A illustrates sewability of optical waveguide devices according to some embodiments. Stretchable fibers and filaments according to this disclosure are compatible with a sewing method that can add sensors to a garment even after construction of the garment. This contrasts with weaving, knitting, or ink-based printing methods which can have difficulty crossing seams. Filaments according to some embodiments may be continuous, shelf-stable filaments that do not require users to do as much materials processing as they do with printer filament. Sewn into athletic tape, sensor fibers may detect muscle stretching when the wearer shifts weight onto the leg, for example. Weight-bearing is an important component of exercise intensity, but weight-bearing status isn't captured by existing motion tracking garments, and camera systems may only do joint angle measurement. Materials and sensors herein may measure surface shape in addition to joint angle to give a more complete picture of muscle effort during body motion. Spatially sensitive optical fibers make possible to calibrate the sensors to individual anatomical landmarks by pressing on references points through the tape or garment.

Figure 10B:
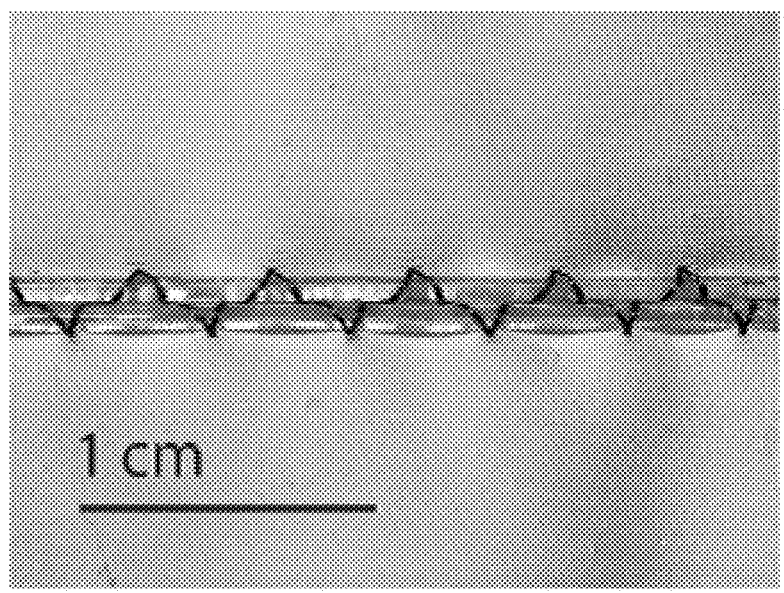
FIG. 10B illustrates a fiber pair sewn on fabric.

FIG. 10B illustrates fiber pair sewn on fabric. Two fibers with solid elastomeric claddings are sewn in parallel and cross-couple light when pressed, leading to a monotonic intensity signal as a function of distance.

Optical waveguides and devices according to the instant disclosure may be prepared or manufactured by a variety of methods. Various porogenic methods may be used to make the spongy elastic material. Some methods involve using sacrificial material that are dissolved out by solvent to form air pockets in an elastomer without dissolving the elastomer itself. A straightforward manufacturing method for nanoporous elastomers is to mix commercially-available silica or polystyrene nanospheres in to the elastomer and then selectively dissolve the microspheres in hydrofluoric acid (for silica) or toluene (for polystyrene) or another solvent that does not dissolve the elastomer. This method has been used to produce elastomeric nanoporous structures for use as compressible photonic crystals (J. Li, Y. Wu, J. Fu, Y. Cong, J. Peng, and Y. Han, "Reversibly strain-tunable elastomeric photonic crystals," *Chem. Phys. Lett.*, vol. 390, no. 1, pp. 285-289, May 2004).

Another sacrificial material is salts. Microscale salt crystals can be produced cheaply at large scale by drowning-out precipitation, then mixed with uncured liquid rubber, then dissolved out by water immersion after curing. However, producing sub-micron salt crystals generally requires surfactants or other chemical, increasing the cost and complexity.

Another manufacturing method is filament extrusion from polymer pellets. Variables such as extrusion speed may be controlled to achieve different desired structural properties. Another manufacturing method is soak-and-stretch processing. Polymer carbonation is a method to form gas pockets that do not need solvents or heating to clear out a sacrificial material.

Different materials and material blends, including but not limited to the use of one or more additives with elastomers, may be used for cores, cladding, jackets, and other elements of exemplary embodiments. Non-limiting examples of materials include paraffin wax and polyethylene glycol with different molecular weights mixed in different ratios. Polymer modifiers and fillers may also be included. Composition parameters which may be controlled include ratio of additive to elastomer and additive size. Mechanical and optomechanical parameters and properties which may be controlled for include but are not limited to density, rheology, strength, optical transmission, and degradation.

Attenuation is but one variable that may be controlled for during the manufacturing process. Some non-limiting examples of attenuation include approximately 0.4 dB/cm, 4.5 to 6 dB/cm, and 0.7 to 2 dB/cm.

Control of the illumination of light sources and receipt and manipulation of signals from detectors in embodiments may be achieved with one or more processors, e.g., of a general purpose computing device. Pressures amounts and locations or positioned may be computed and output to a storage medium or to a user, e.g., a human user, or some other device. Methods described herein may be executed using computer program code stored in a storage medium and executed by one or more processors.

Some embodiments may be a system, a method, and/or a computer program product. The computer program product may include a computer readable storage medium (or media) having computer readable program instructions thereon for causing a processor to carry out aspects of this disclosure.

A computer readable storage medium may be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions for carrying out operations may be assembler instructions, instruction-set-architecture (ISA) instructions, machine instructions, machine dependent instructions, microcode, firmware instructions (instructions embedded in firmware), state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present disclosure are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, can be implemented by computer readable program instructions.

Computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Where a range of values is provided in this disclosure, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be separated from or combined with the features of any of the other several embodiments without departing from the scope or spirit of the present invention. Recited methods may also carried out in the order of events recited or in any other order which is logically possible.

While exemplary embodiments of the present invention have been disclosed herein, one skilled in the art will recognize that various changes and modifications may be made without departing from the scope of the invention as defined by the following claims.

What is claimed is:

1. An optical waveguide device, comprising:
   a first waveguide core;
   a second waveguide core;
   a spongy elastic material with compressible gas pockets therein, wherein the spongy elastic material has a refractive index which changes when the spongy elastic material is compressed, bent, or stretched, wherein the spongy elastic material is positioned between the first and second waveguide cores, wherein radiant energy in the first waveguide core escapes to the second waveguide core through the spongy elastic material depending on the refractive index of the spongy elastic material; and
   a detector which detects from the second waveguide core a signal intensity which depends on the radiant energy that escapes the first waveguide core through the spongy elastic material when the spongy elastic material is compressed, bent, or stretched.

2. The optical waveguide device of claim 1, wherein the optical waveguide device is a spatial-sensing pressure feedback device.

3. The optical waveguide device of claim 2, wherein the detector is arranged to measure a back-reflected signal in the second waveguide core, wherein an intensity of the back-reflected signal varies in dependence on a spatial position where the spongy elastic material is compressed, bent, or stretched.

4. The optical waveguide device of claim 1, wherein radiant energy in the first waveguide core is sent along a first path, wherein a fraction of radiant energy in the first core that escapes to the second core is sent along a new path by the second waveguide core.

5. The optical waveguide device of claim 4, wherein the first and second waveguide cores and the respective paths the cores define for radiant energy are non-parallel.

6. The optical waveguide device of claim 1, wherein the pockets are sub-micron pores.

7. The optical waveguide device of claim 6, wherein the spongy elastic material is a nanoporous elastomer.

8. The optical waveguide device of claim 1, wherein the first and second waveguide cores are cores of respective first and second optical fibers, and wherein the spongy elastic material is a cladding shared by the first and second optical fibers.

9. The optical waveguide device of claim 8, wherein the first and second optical fibers are parallel.

10. The optical waveguide device of claim 1, wherein the first and second waveguide cores and the spongy elastic material therebetween are all planar.

11. The optical waveguide device of claim 10, wherein the first and second waveguide cores and the spongy elastic material therebetween are thin films.

12. The optical waveguide device of claim 1, further comprising
   a first detector which detects a first signal intensity at a far end of the first waveguide core, wherein the detector which detects from the second waveguide core detects a second signal intensity at a near end of the second waveguide core;
   one or more processors for determining a longitudinal position at which the radiant energy escapes the first waveguide core to the second waveguide core based on the first and second detected signal intensities,
   wherein the position at which the radiant energy escapes corresponds with a position of external pressure.

13. A method of pressure mapping of externally applied pressure with an optical waveguide device, comprising
   detecting with a first detector a first signal intensity at a far end of a first waveguide core;
   detecting with a second detector a second signal intensity at a near end of a second waveguide core, wherein the first and second waveguide cores are coupled in parallel with one another with a spongy elastic material positioned between the first and second waveguide cores, wherein the spongy elastic material has a refractive index which changes when the spongy elastic material is compressed, bent, or stretched, wherein radiant energy in the first waveguide core escapes to the second waveguide core through the spongy elastic material depending on the refractive index of the spongy elastic material; and determining a longitudinal position at which radiant energy escapes the first waveguide core to the second waveguide core based on the first and second detected signal intensities, wherein the position at which the radiant energy escapes corresponds with the position of externally applied pressure.

14. An optical waveguide device, comprising:

a first group of waveguide cores arranged in rows in a first geometric plane;

a second group of waveguide cores arranged in columns in a second geometric plane spaced apart from the first geometric plane;

a spongy elastic material with compressible gas pockets therein, wherein the spongy elastic material has a refractive index which changes when the spongy elastic material is compressed, bent, or stretched, wherein the spongy elastic material is positioned between the first and second groups of waveguide cores, wherein radiant energy in the first group escapes to the second group through the spongy elastic material depending on the refractive index of the spongy elastic material; and one or more detectors arranged to detect changes in one or more signal intensities in the second group of waveguide cores which depend on the radiant energy that escapes the first group through the spongy elastic material when the spongy elastic material is compressed, bent, or stretched.

15. The optical waveguide device of claim 14, further comprising one or more processors configured to cause sequential illumination of waveguide cores in the first group one at a time, determine a spatial position where the spongy elastic material is compressed, bent, or stretched based on a first signal intensity from a waveguide core from the first group that is illuminated and a second signal intensity from a waveguide core from the second group for which a change in signal intensity is detected.

* * * * *